(12) United States Patent
Yu et al.

(10) Patent No.: US 12,245,944 B1
(45) Date of Patent: Mar. 11, 2025

(54) METHOD FOR PREPARING A HETEROGENEOUS METAL COMPOSITE STRUCTURE FOR MEDICAL IMPLANTATION

(71) Applicant: Jilin University, Jilin (CN)

(72) Inventors: Zhenglei Yu, Jilin (CN); Renlong Xin, Jilin (CN); Haojie Chi, Jilin (CN); Delong Gao, Jilin (CN); Zezhou Xu, Jilin (CN); Yunting Guo, Jilin (CN); Long Ma, Jilin (CN); Yanan Yang, Jilin (CN); Pengwei Sha, Jilin (CN); Jincheng Wang, Jilin (CN); Xin Zhao, Jilin (CN); He Liu, Jilin (CN)

(73) Assignee: Jilin University, Changchun (CN)

( * ) Notice: Subject to any disclaimer, the term of this patent is extended or adjusted under 35 U.S.C. 154(b) by 0 days.

(21) Appl. No.: 18/811,762

(22) Filed: Aug. 21, 2024

(51) Int. Cl.
| | |
|---|---|
| *A61F 2/30* | (2006.01) |
| *B22F 7/02* | (2006.01) |
| *B22F 10/28* | (2021.01) |
| *B22F 10/60* | (2021.01) |
| *B23K 26/342* | (2014.01) |

(Continued)

(52) U.S. Cl.
CPC ............. *A61F 2/3094* (2013.01); *B22F 7/02* (2013.01); *B22F 10/60* (2021.01); *B23K 26/342* (2015.10); *B33Y 10/00* (2014.12); *B33Y 40/20* (2020.01); *B33Y 70/00* (2014.12); *B33Y 80/00* (2014.12); *A61F 2002/30263* (2013.01); *A61F 2002/3092* (2013.01); *A61F 2002/30968* (2013.01); *A61F 2002/3097* (2013.01); *A61F 2310/00023* (2013.01); *A61F 2310/00041* (2013.01); *B22F 10/28* (2021.01); *B22F 2301/058* (2013.01); *B22F 2301/205* (2013.01)

(58) Field of Classification Search
CPC ............... B01D 46/70; B60H 1/00378; B60H 2001/00099; B60H 3/0625; B60H 3/0633; Y02A 50/2351; A61F 2/3094; A61F 2002/30263; A61F 2002/3092; A61F 2002/30968; A61F 2002/3097; A61F 2310/00023; A61F 2310/00041; B33Y 10/00; B33Y 70/00; B33Y 80/00; B33Y 40/20; B23K 26/342; B22F 10/60; B22F 7/02; B22F 10/28; B22F 2301/058; B22F 2301/205
USPC ...................................... 219/76.14
See application file for complete search history.

(56) References Cited

FOREIGN PATENT DOCUMENTS

| CN | 110773739 | * | 2/2020 |
| CN | 110773739 A | | 2/2020 |

(Continued)

*Primary Examiner* — Dana Ross
*Assistant Examiner* — Joseph W Iskra

(57) ABSTRACT

Disclosed is a method for preparing a heterogeneous metal composite structure for medical implantation, including the steps of: step 1, preparing titanium alloy powder into a porous skeleton according to different printing strategies; step 2, filling magnesium after being melted into pores of the porous skeleton; and step 3, cooling a titanium-magnesium interpenetrating phase composite structure prepared in step 2 to room temperature, and covering a surface of the titanium-magnesium interpenetrating phase composite structure with a hydroxyapatite coating. In the present disclosure, a porous lattice dot-array structure of titanium alloy is used as a skeleton, and the skeleton pore is filled by pressureless infiltration of magnesium or hot isostatic pressure.

5 Claims, 5 Drawing Sheets

(51) Int. Cl.
*B33Y 10/00* (2015.01)
*B33Y 40/20* (2020.01)
*B33Y 70/00* (2020.01)
*B33Y 80/00* (2015.01)

(56) References Cited

FOREIGN PATENT DOCUMENTS

| | | | |
|---|---|---|---|
| CN | 111250703 | * | 6/2020 |
| CN | 111250703 A | | 6/2020 |

* cited by examiner

METHOD FOR PREPARING A HETEROGENEOUS METAL COMPOSITE STRUCTURE FOR MEDICAL IMPLANTATION

CROSS-REFERENCE TO RELATED APPLICATIONS

This application claims priority of Chinese Patent Application No. 202311049592.1, filed on Aug. 21, 2023, the entire contents of which are incorporated herein by reference.

TECHNICAL FIELD

The present disclosure relates to the technical field of medical implant prosthesis, and specifically relates to a method for preparing a heterogeneous metal composite structure for medical implantation.

BACKGROUND

Pelvis is an important osseous structure connecting a trunk and limbs of human body. With the frequent occurrence of traffic accidents and natural disasters, more and more incidents occur that accidentally lead to pelvic bone damage or even permanent trauma. With the organ degeneration and orthopedic diseases caused by population aging, how to more efficiently and quickly perform bone repair and bone replacement for pelvic bone and hip joint has become a hot issue in clinical medicine.

Common medical implant alloys, such as titanium alloy and magnesium alloy, are medical bone implant materials with good biocompatibility, but at present, there are shortcomings and deficiencies. Although the titanium alloy has high strength, it is inert metal, and has poor bone-promoting property and long bone-forming period after being implanted into human body. Although the magnesium alloy has good bone-promoting activity, it is easy to degrade and cannot exist for a long time after being implanted into human body. Therefore, how to effectively combine the advantages of various materials and avoid the shortcomings will become the main research direction of medical implants in the future.

In addition, according to the natural bone standard of 2022, an implant for pelvic bone and hip joint replacement is to have a Young's modulus of reaching 10 Gpa-20 Gpa and strength of more than 180 Mpa. However, Young's moduli of the titanium alloy and the magnesium alloy is 113.8 Gpa and 45 Gpa, respectively, which far exceed the Young's modulus standard of natural bone, resulting in a "stress shielding" behavior, thereby leading to bone atrophy without postoperative exercise. However, according to the existing research, a traditional titanium alloy-magnesium alloy composite structure prepared by hot spinning and microwave sintering can reach more than 180 Mpa in compressive strength, but the Young's modulus is greatly reduced to 3 Gpa-8G pa, which cannot meet the requirements of pelvic bone strength. Therefore, it is particularly important to prepare the titanium alloy-magnesium alloy composite structure by what suitable process to eliminate the "stress shielding" and retain the strength.

Pelvic bone is often exposed to the risk of secondary damage due to external impacts after bone repair and bone replacement surgery, while the existing orthopedic implant preparation methods, such as traditional processing techniques: casting or machining, require customized molds or cutting large amounts of raw materials, and are expensive to produce for a single piece or a small amount of high-precision products. With the additive manufacturing process, time and cost can be significantly reduced.

In conclusion, it is necessary to prepare an alloy skeleton by the additive manufacturing technology and compositely strengthen the titanium alloy and the magnesium alloy by appropriate processing means to finally form a heterogeneous metal composite structure for medical implantation which can meet medical requirements.

SUMMARY

In view of the "stress shielding" phenomenon and the multi-material bonding strength problem of the above-mentioned medical metal implant materials in the human body, the present disclosure innovatively provides a titanium-magnesium interpenetrating phase structure. A titanium-alloy crystal lattice structure satisfying the mechanical properties of various regions of pelvic bone is prepared as a skeleton by additive manufacturing, and pores of the skeleton are filled by means of magnesium pressureless infiltration or hot isostatic pressing to complete the preparation. A Young's modulus of the prepared titanium-magnesium interpenetrating phase composite structure can be regulated by controlling a porosity of the crystal lattice structure. The Young's modulus is in a range of 10 vGpa-20G pa, and a compressive strength can reach more than 180 Mpa, meeting the requirements of pelvic bone repair and hip joint replacement. The prepared titanium-magnesium interpenetrating phase composite structure adds a layer of hydroxyapatite coating on the surface. The presence of hydroxyapatite coating effectively delays the degradation of magnesium and further promotes the formation of damaged bone.

To achieve the above objective, the present disclosure provides the following technical solutions.

A method for preparing a heterogeneous metal composite structure for medical implantation, including the steps of:
- step 1, preparing, based on a selective laser melting technique or a laser powder bed fusion technique, titanium alloy powder into a porous skeleton according to different printing strategies;
- step 2, filling magnesium after being melted into pores of the porous skeleton; and
- step 3, cooling a titanium-magnesium interpenetrating phase composite structure prepared in step 2 to room temperature, and covering a surface of the titanium-magnesium interpenetrating phase composite structure with a hydroxyapatite coating.

Preferably, in step 1, the porous skeleton is prepared using the selective laser melting technique by the following specific method: purging, before printing, a material molding chamber of a selective laser melting device with high-purity argon gas until oxygen content in the molding chamber is less than 0.1%, preheating a print substrate to 200° C., ensuring the dimensional accuracy for printing the porous skeleton, continuously printing the titanium alloy powder with a median diameter of 35 μm in layers using the selective laser melting technique under the conditions of a laser power of 100 W, a laser scanning speed of 1200 mm/s, and a layer thickness of 30 μm.

Preferably, in step 2, the specific method for filling magnesium after being melt into pores of the porous skeleton is as follows: placing the printed porous skeleton on a stainless steel mold, placing a magnesium block on the porous skeleton in a smooth manner, and placing the stainless steel mold on a fixing apparatus in a graphite resistance furnace, to complete the preparatory work before the infiltration, wherein it is ensured that an actual height of the stainless steel mold is higher than a plane of the magnesium block, the graphite resistance furnace is heated to 800° C. by heating in the flow of argon for 10 min, during which, the molten magnesium block flows into the pores of the porous skeleton by its own gravity in the absence of external loads, and is cooled in the graphite resistance furnace to complete the infiltration process.

Preferably, in step 1, the specific method for preparing the porous skeleton by using laser powder bed fusion technique is as follows: processing titanium alloy powder with a median diameter of 35 μm by adopting the laser powder bed fusion technique with a laser powder bed device with process parameters of a scanning speed of 1,200 mm/s and a laser power of 155 W, reducing, during the scanning process, a thermal stress between two adjacent layers by using a sawtooth pattern, and alternating a scanning angle by 90° on a previous layer.

Preferably, in step 2, the specific method for filling magnesium after being melt into pores of the porous skeleton is as follows: placing the prepared porous skeleton in an alumina ceramic mold, evenly sprinkling the magnesium powder inside pores of the porous skeleton, allowing the magnesium powder to be fully filled into internal pores of the porous skeleton by means of mechanical vibration, smoothly placing the alumina ceramic mold in a hot isostatic pressing sintering furnace, vacuuming the hot isostatic pressing sintering furnace and introducing argon gas, mixing the porous skeleton and the magnesium powder using a hot isostatic pressing process, and heating the hot isostatic pressing sintering furnace in an argon environment in the pressure of 150 Mpa for 4 h to 900° C., heating 150 MPa pressure for 4 hours, the magnesium powder being melted during the heating, and being closely adhered to the porous skeleton under the pressure and temperature.

Preferably, in step 3, the specific method for covering a surface of the titanium-magnesium interpenetrating phase composite structure with a layer of hydroxyapatite coating is as follows: preparing the hydroxyapatite coating using an electrophoretic deposition method; and using the prepared titanium-magnesium interpenetrating phase composite structure as a negative electrode, and an inert electrode graphite sheet as a positive electrode, with two pole sheets of negative electrode and positive electrode kept parallel and a distance between the negative electrode and the positive electrode being at 20 mm, vertically inserting the titanium-magnesium interpenetrating phase composite structure into a quartz glass beaker with an HA suspension, adding 2% of a volume fraction of concentrated nitric acid as an electrolyte, adjusting a pH value with ammonia to stabilize the pH value at the range of 4-6, performing electrolytic deposition under a constant-voltage mode for a certain period of time under a set voltage, covering the surface of the titanium-magnesium interpenetrating phase composite structure as the negative electrode by the hydroxyapatite coating during deposition, closing a power source after the surface of the titanium-magnesium interpenetrating phase composite structure is completely covered with the hydroxyapatite coating, and taking out a sample for drying.

Preferably, in step 1, the porous skeleton has a lattice dot-array structure.

Preferably, in step 1, the lattice dot-array structure is a body-centered cubic dot-array structure, a closed tetragonal beam-0 type structure or a closed arc beam-0 type structure.

Preferably, in step 1, the body-centered dot-array structure is a hexahedron with eight vertices as key nodes, which are connected to each other to form external beams, and centers of the six faces serve as nodes of internal beams, and the internal beams are connected to and combined with the external beams to form a body-centered cubic structure.

Preferably, in step 1, the closed tetragonal beam-0 type structure is based on a face-centered lattice to construct diagonal X-beams, middles of which are fixed using straight columns, and a base configuration is constructed by mirroring 2-3 times, joints between the diagonal X-beams are at the face centers of each plane, and the closed tetragonal beam-0 type structure is built by regulating a total horizontal length a and a vertical length b.

Preferably, in step 1, the closed arc beam-O type structure is based on a quadrilateral, with four sides cut with circular arcs, constructing arc beams for circular arrays to establish the closed arc beam-0 type structure, in which a horizontal arc diameter C1 and a vertical arc C2 are used as variable parameters to regulate the porosity of the closed arc beam-0 type structure.

Compared with the prior art, the present disclosure has the following beneficial effects.

A preparation process of a traditional composite material is a simple combination of various phase materials, which has limited improvement in the mechanical properties of the material itself. The titanium-magnesium interpenetrating phase composite structure prepared in the present disclosure, similar to a pearl layer-like structure, can be subdivided into a soft phase region, a hard phase region and a bonding region, with a good bonding interface. The existence of a soft phase and a hard phase can have a stable deformation when resisting impacts and a strong damping capacity, which can effectively avoid secondary damage after surgery.

Unlike porous titanium-magnesium interpenetrating phase composite structures prepared by conventional processes such as hot spinning, microwave sintering, and titanium filament winding and soaking, the additive manufacturing technology used in the present disclosure is more convenient and faster, greatly reducing the time and economic cost. A specific design is performed according to different positions of pelvic bone, achieving the "coupling" effect between structures through ingenious splicing and combination, and further improving the impact resistance.

In the present disclosure, the titanium-magnesium interpenetrating phase composite structure is innovatively applied to the field of medical pelvic bone implantation, two kinds of metals with great difference in mechanical properties are combined by means of additive manufacturing and pressureless infiltration or hot isostatic pressing, and the combination interface is stable. The prepared titanium-magnesium interpenetrating phase composite structure combines the advantages of the two, makes up for the deficiency of a single material, makes full use of the strength of titanium alloy and the bone-promoting activity of magnesium, and solves the problem of "stress shielding" which has long been criticized in clinical medicine without changing the good biocompatibility of medical implants, so that a rejection reaction does not occur with natural bones after implantation.

The hydroxyapatite coating is added on the surface of the prepared titanium-magnesium interpenetrating phase composite structure, which not only effectively slows down the degradation of magnesium, but also promotes the development and growth of chondrocytes and the formation of bone trabeculae. In combination with the porous structure, the growth of bone cells and the healing of bone tissues are further promoted, which effectively alleviates the excessive degradation of the implant in the human body and shortens an osteogenic cycle, thereby alleviating the pain of patients.

1—magnesium block; 2—porous skeleton; 3—stainless steel mold; 4—fixing apparatus; 5—graphite resistance furnace; 6—selective laser melting device; 7—titanium alloy powder; 8—hot isostatic pressure sintering furnace; 9—magnesium powder; 10—alumina ceramic mold; 11—laser powder bed device; 120—hard-phase zone; 121—soft-phase zone; and 122—bonding zone.

DETAILED DESCRIPTION

In order to better illustrate the preparation process involved in the present disclosure and the advantages over the prior art, further explanations will be given on the basis of the above-described accompanying drawings.

Figure 1:
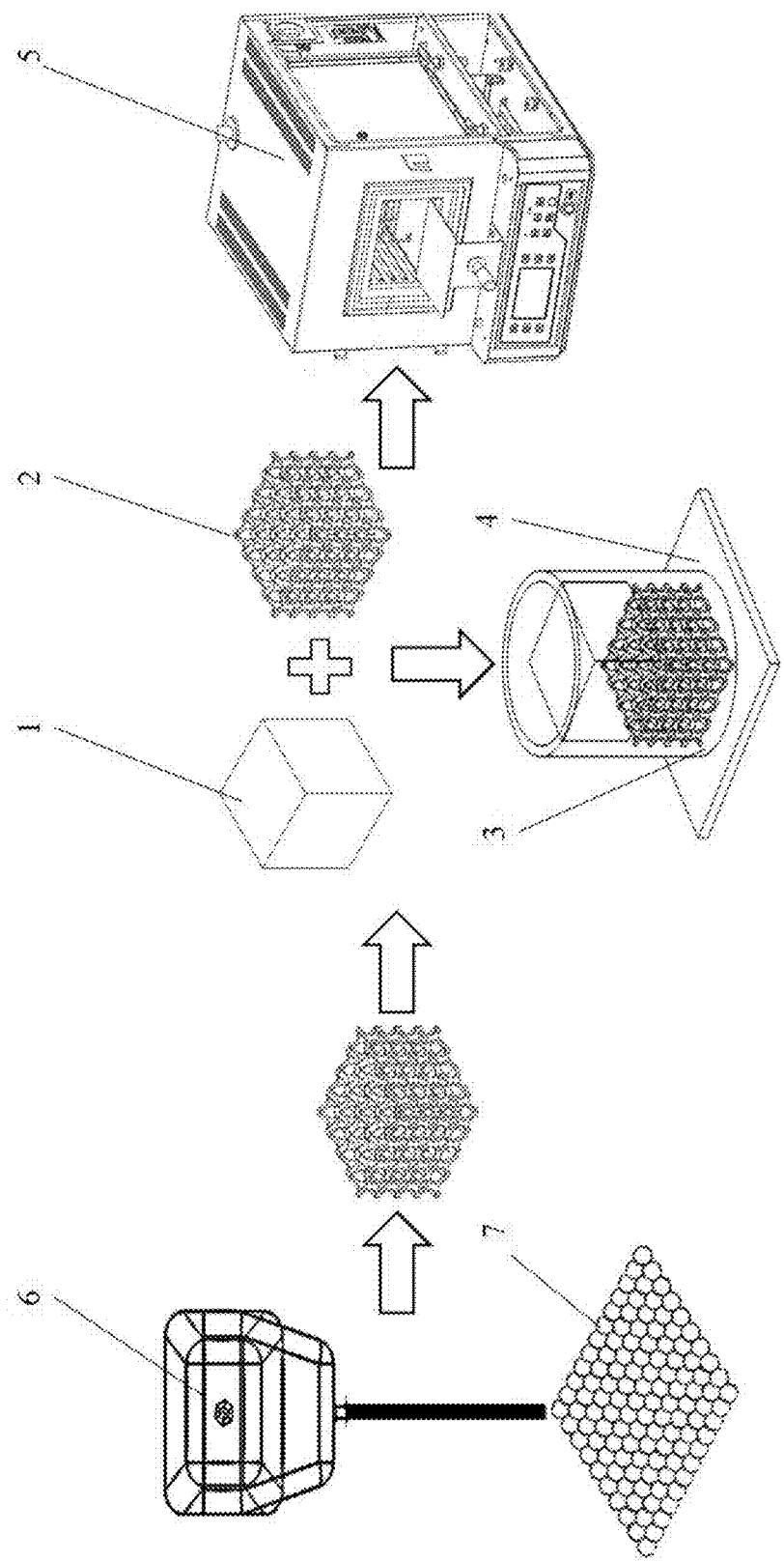
FIG. 1 is a flow chart of the preparation of a titanium-magnesium interpenetrating phase composite structure by pressureless infiltration.
Figure 2:
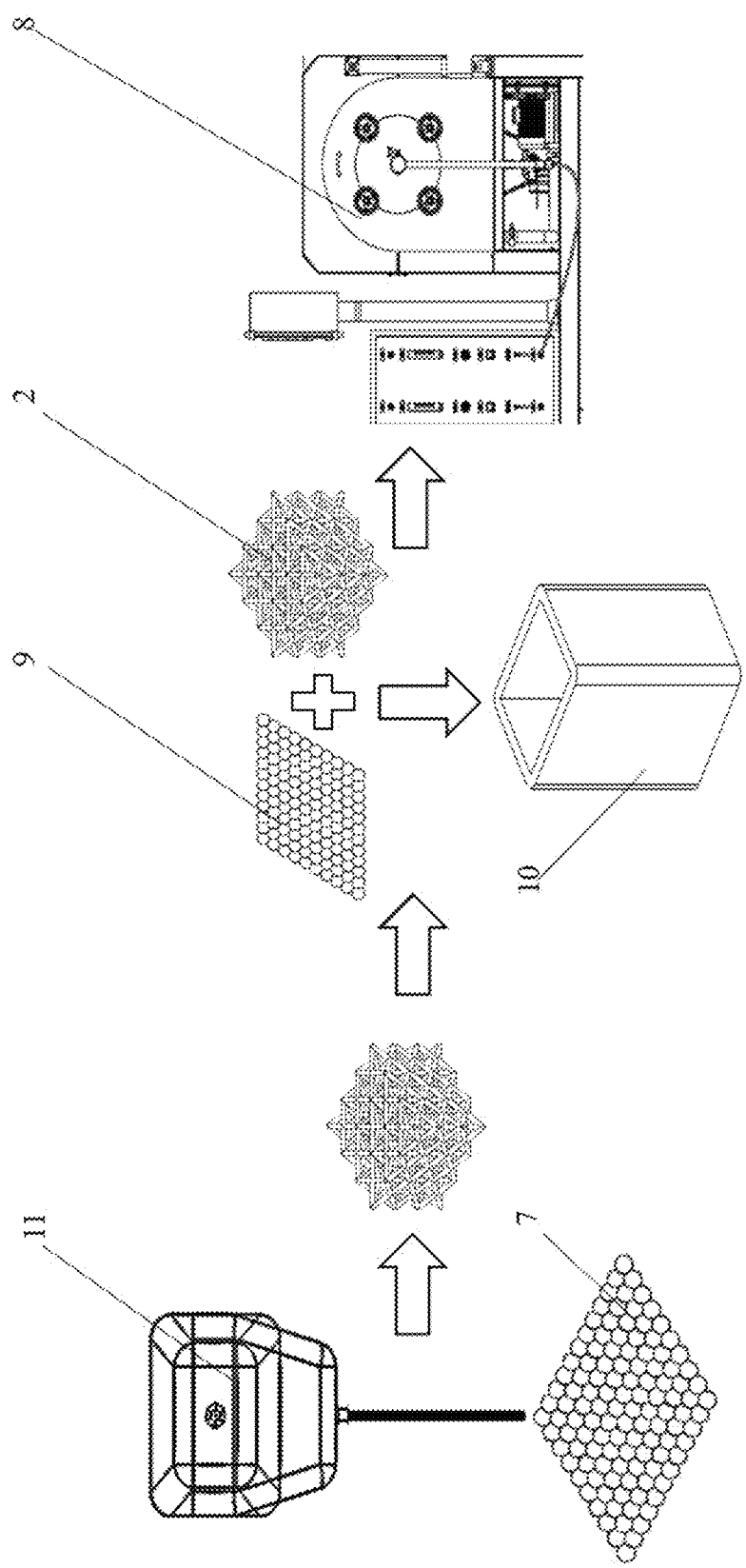
FIG. 2 is a flow chart of the preparation of a titanium-magnesium interpenetrating phase composite structure by hot isostatic pressing.
Figure 3:
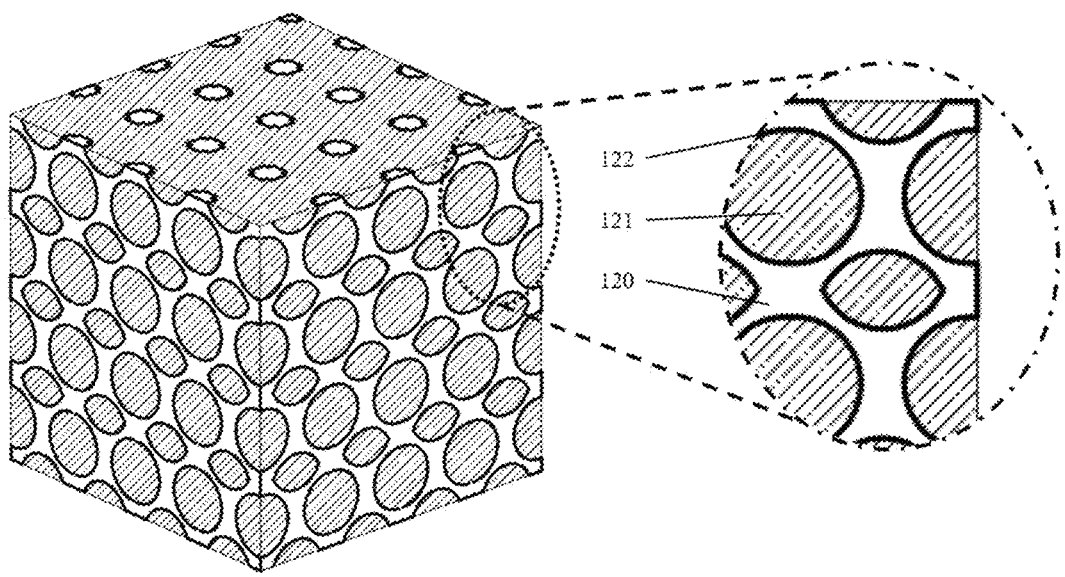
FIG. 3 is an effect diagram of a formed titanium-magnesium interpenetrating phase composite structure.

Referring to FIGS. 1-3, a method for preparing a heterogeneous metal composite structure for medical implantation includes the following steps.

In step 1, based on a selective laser melting technique or a laser powder bed fusion technique, titanium alloy powder 7 is prepared into a porous skeleton 2 according to different printing strategies.

In step 2, magnesium after being melted is filled into pores of the porous skeleton 2.

In step 3, a titanium-magnesium interpenetrating phase composite structure prepared in step 2 is cooled to room temperature, and a surface of the titanium-magnesium interpenetrating phase composite structure is covered with a hydroxyapatite coating.

Preferably, in step 1, the porous skeleton is prepared using the selective laser melting technique by the following specific method: purging, before printing, a material molding chamber of a selective laser melting device with high-purity argon gas until oxygen content in the molding chamber is less than 0.1%, preheating a print substrate to 200° C., ensuring the dimensional accuracy for printing the porous skeleton, continuously printing the titanium alloy powder with a median diameter of 35 μm in layers using the selective laser melting technique under the conditions of a laser power of 100 W, a laser scanning speed of 1200 mm/s, and a layer thickness of 30 μm.

Referring to FIG. 1, in S1, a specific method for preparing the porous skeleton 2 using the selective laser melting technique is as follows: prior to printing, the material forming chamber of the selective laser melting device 6 is purged with high-purity argon gas until the oxygen content in the forming chamber is less than 0.1% to reduce oxidation; the printing substrate is preheated to 200° C. to reduce the residual stress, avoid cracking and ensure good dimensional accuracy of the printing porous skeleton 2; and the titanium alloy powder 7 with a median diameter of about 35 μm is continuously printed in layers by the selective laser melting technique under the conditions of a laser power of 100 W, a laser scanning speed of 1200 mm/s and a layer thickness of 30 μm.

Referring to FIG. 1, in S2, a specific method for filling the inside of the pores of the porous skeleton 2 after the magnesium is melted is as follows: a pressureless infiltration method is used, the printed porous skeleton 2 is placed on a stainless steel mold 3, a magnesium block 1 (with a purity of up to 99.99%) is placed on the porous skeleton 2 smoothly, the stainless steel mold 3 is placed on a fixing device 4 in a graphite resistance furnace 5 to complete preparation before infiltration, the actual height of the used stainless steel mold 3 needs to be ensured to be higher than the plane of the magnesium block 1 to avoid infiltration outside the stainless steel mold 3 during melting process, and finally, the graphite resistance furnace 5 is heated to 800° C. (namely, 150° C. higher than the melting point of magnesium), and heated in a flowing argon gas for 10 minutes; and during this time, the molten magnesium block 1 flows into the pores of the porous skeleton 2 by its own weight without an external load, cools and completes the infiltration process in the graphite resistance furnace 5, and the porous skeleton 2 and the magnesium block 1 are ultrasonically cleaned with acetone to reduce contamination before the magnesium block 1 is combined with the titanium alloy powder 7.

Referring to FIG. 2, in S1, a specific method for preparing the porous skeleton 2 using the laser powder bed laser powder bed fusion technique is as follows: the titanium alloy powder 7 with a median diameter of about 35 m is processed by a laser powder bed laser powder bed fusion technique using a laser powder bed apparatus 11 at a scanning speed of 1200 mm/s and a laser power of 155 W. In the scanning process, a zigzag pattern is used to reduce the thermal stress between two adjacent layers, and the scanning angle is alternated by 90° on the previous layer, so as to prepare a porous skeleton 2 as shown in FIG. 2.

Referring to FIG. 2, in S2, a specific method for filling an inside of the pores of the porous skeleton 2 after the magnesium is melted is as follows: the prepared porous skeleton 2 is placed in an alumina ceramic mold 10 by a hot isostatic pressing method, magnesium powder 9 is fully sprinkled into the pores of the porous skeleton 2, and the magnesium powder 9 is further fully filled into the internal pores of the porous skeleton 2 by means of mechanical vibration; and finally, the alumina ceramic mold 10 is placed in a hot isostatic pressing sintering furnace 8 in a stable manner, and the inside of the hot isostatic pressing sintering furnace 8 is evacuated and then argon is introduced. In order to form a dense and massive metal composite material, the porous skeleton 2 and the magnesium powder 9 are mixed by the hot isostatic pressing process, the hot isostatic pressing sintering furnace 8 is heated to 900° C. in an argon environment and heated for 4 hours under a pressure of 150 MPa, and during the heating process, the magnesium powder 9 melts and is tightly adhered to the porous skeleton 2 under the action of pressure and temperature.

Referring to FIG. 3, in S3, the titanium-magnesium interpenetrating phase composite structure can be subdivided into a soft phase region 121, a hard phase region 120, and a bonding region 122. In the face of impact, the hard phase region 120 bears more load due to the larger Young modulus and better mechanical properties of the material. However, in the bonding region 122, due to the interpenetration of the two materials in the preparation process, MgAl, $Ti_2Si_3$ and other phases will appear, and the bearing capacity of the bonding region 122 is slightly weak, mainly playing the role of stable deformation; and however, the magnesium phase in the soft phase region 121 plays a role of transition and connection, its bearing capacity is weaker than the former two phases, and the first crack occurs when it encounters severe impact. The overall three-dimensional interpenetrating phase structure, combined with the bionic concept, imitates the pearl layer brick-mud structure, its "soft and hard" characteristics can greatly improve the structure and material synergy, not only greatly reduce the Young modulus, eliminate the "stress shielding", but also ensure the Young modulus between 10 Gpa-20 Gpa, strength over 180 Mpa, in line with human bone implantation requirements.

In S3, a specific method for covering the surface of the titanium-magnesium interpenetrating phase composite structure with a layer of hydroxyapatite coating is as follows: hydroxyapatite coating is prepared by electrophoretic deposition; and the prepared titanium-magnesium interpenetrating phase composite structure is used as a cathode, an inert electrode graphite sheet is used as an anode, the cathode-anode two pole pieces are kept in parallel and the cathode-anode two pole spacing is kept at 20 mm, and vertically inserted into a quartz glass beaker filled with a certain concentration of HA suspension, concentrated nitric acid with a volume fraction of about 2% is added as electrolyte, and the pH value is adjusted with ammonia water to stabilize the pH value between 4 and 6; and a constant voltage mode is used to perform electrophoretic deposition at a set voltage for a certain time, and during the deposition, the hydroxyapatite coating will gradually cover the surface of the titanium-magnesium interpenetrating phase composite structure as a cathode. After the hydroxyapatite coating completely covers the surface of the titanium-magnesium interpenetrating phase composite structure, the power supply is turned off, and the sample is taken out and placed in an environment with a higher relative humidity and a lower relative temperature for drying.

Referring to FIGS. 1-8, in S1, the porous skeleton 2 is a lattice lattice structure.

Figure 4:
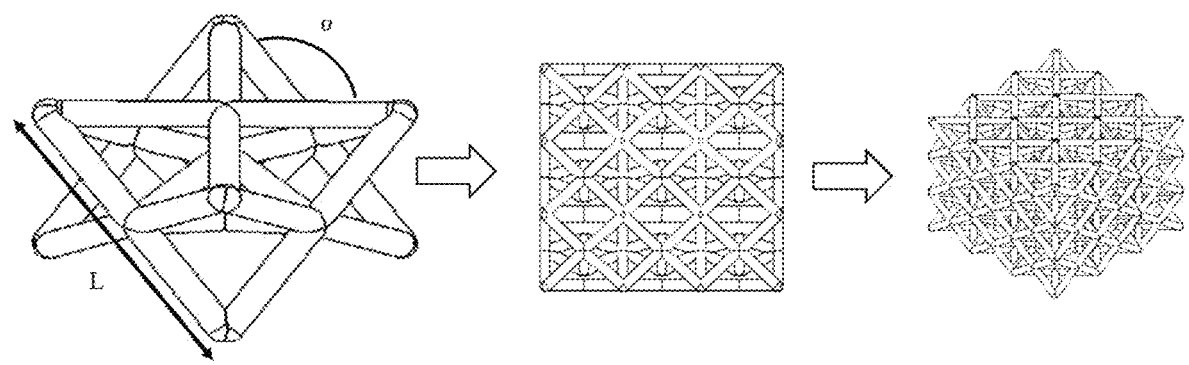
FIG. 4 is a schematic diagram of a body-centered cubic lattice structure.
Figure 5:
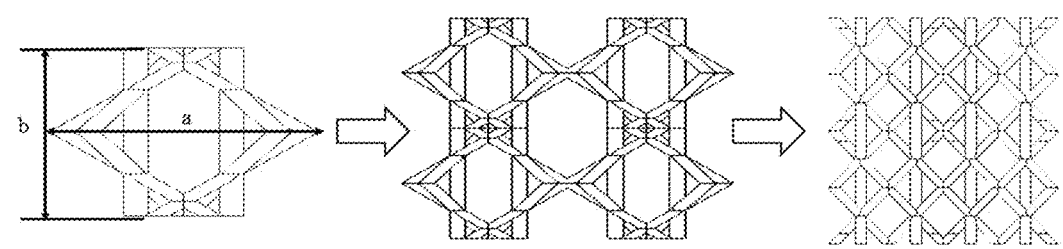
FIG. 5 is a schematic diagram of a closed square beam-0 configuration structure.
Figure 6:
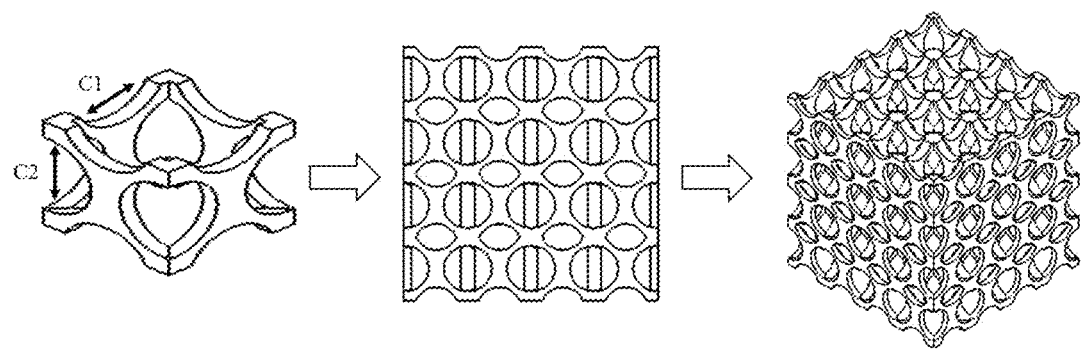
FIG. 6 is a schematic diagram of a closed curved beam-0 configuration structure.

Referring to FIGS. 4-6, in S1, the lattice lattice structure is a body-centered cubic lattice structure, a closed square beam-0 type structure, or a closed arc beam-0 type structure.

Referring to FIG. 4, in S1, the body-centered cubic lattice structure takes eight vertices of a hexahedron as key nodes, which are connected to each other to form an outer beam, and takes face-centered positions of six faces as inner beam nodes, and the inner beam and the outer beam are connected and combined to form the body-centered cubic structure.

Referring to FIG. 5, in S1, the closed square beam-0 type structure is based on a face-centered lattice to construct an italics X-shaped beam, the middle of the italics X-shaped beam is fixed by a straight column, and a base configuration is constructed by 2-3 times of mirror images, the connection between each of the italics X-shaped beams is the face-centered position of each plane, and the closed square beam-0 type structure is established by adjusting the total horizontal length a and the vertical length b.

Referring to FIG. 6, in S1, the closed arc-shaped beam-0 structure is based on a quadrilateral, and four sides are cut with an arc to construct an arc-shaped beam and form a circular array to establish the closed arc-shaped beam-0 structure, the porosity of the closed arc-shaped beam-0 structure is regulated with the horizontal arc diameter C1 and the vertical arc C2 as variable parameters.

Referring to FIG. 1 or FIG. 2, the titanium alloy powder 7 used in S1 is Ti-6Al-4V powder.

Figure 7:
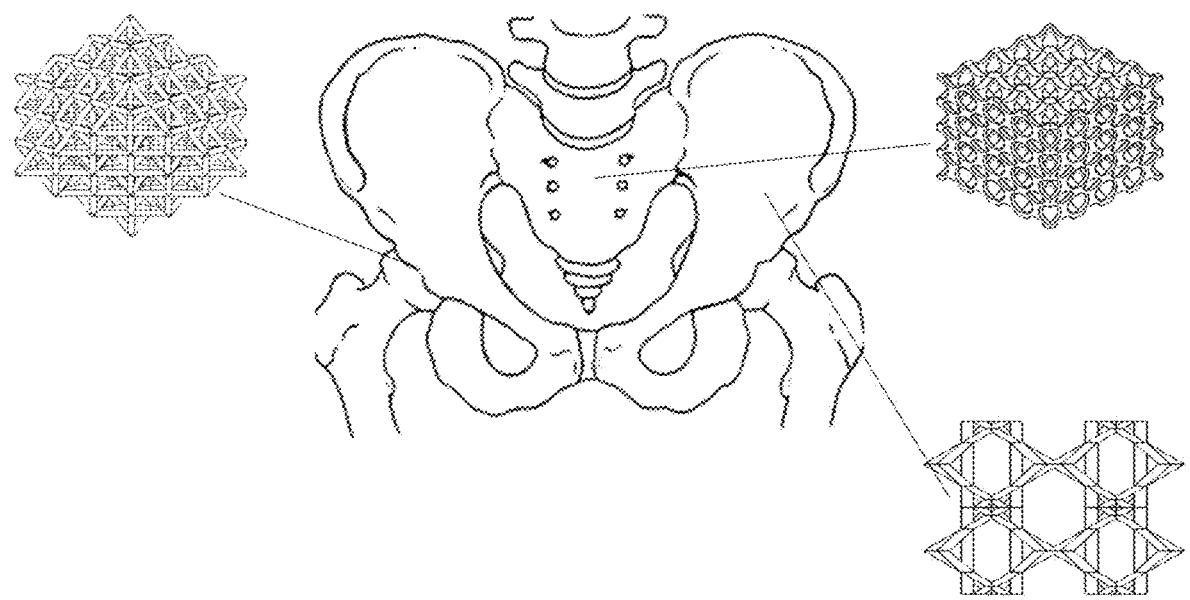
FIG. 7 is a schematic diagram of a crystal lattice designed specifically for different positions of pelvic bone.

Referring to FIG. 7, in S1, the body-centered cubic lattice structure is arranged in an acetabular region.

Referring to FIG. 7, in S1, the closed square beam-0 type structure is arranged in a iliac region.

Referring to FIG. 7, in S1, the closed arc beam-0 type structure is arranged in a sacral region.

The present invention includes the following operation principles.

Pelvis can be considered as a three-dimensional columnar structure formed by multiple bone connections, which can be subdivided into the posterior sacrum, coccyx and bilateral arc-shaped hip bone according to different positions, which is mainly used for bearing load, connecting and protecting internal organs in human body. Once the pelvic bone is damaged due to severe impact, the action of a person will be greatly limited. Therefore, in the completion of bone repair and bone replacement, it is necessary to pay attention to the impact resistance and vibration damping performance of implanted bone so as to avoid secondary postoperative trauma. At the same time, according to the existing research, when the pelvic bone is impacted, the stress mainly passes through the sacroiliac joint from the upper end of the sacrum and then passes along the lower edge of the ilium, the stress distribution on both sides is mainly distributed near the greater notch of the ischium, the stress around is small, and finally the stress is transmitted to the acetabulum and anterior ring region on both sides. Obviously, different regions of the pelvic bone are subjected to different forces when they face the impact. So far, it is difficult to simultaneously meet the force-bearing standard of multiple regions of the pelvic bone by designing a single lattice lattice structure. Therefore, as shown in FIG. 7, the idea of designing and filling the lattice lattice structure specifically according to different positions of the pelvic bone is put forward. A variety of lattice lattice structures suitable for different impact conditions as shown in FIGS. 4-6 can be prepared by printing, and filled according to different stress regions of the pelvis, for example, the closed arc-shaped beam-O structure has the largest bearing capacity among the three lattice structures, and can be set in the sacral region where the pelvis first encounters impact load; similarly, the body-centered cubic lattice structure has good vibration damping performance and can be set in the acetabular region; and the closed tetragonal beam-0 construct is stable in deformation and can effectively transmit loads, and can be placed in the iliac region to join the sacral and acetabular regions. Due to the different filling positions, the lattice lattice structures of the three regions play the role of mechanical locking, which can make full use of advantages thereof and make up for the deficiency of a single structure.

Figure 8:
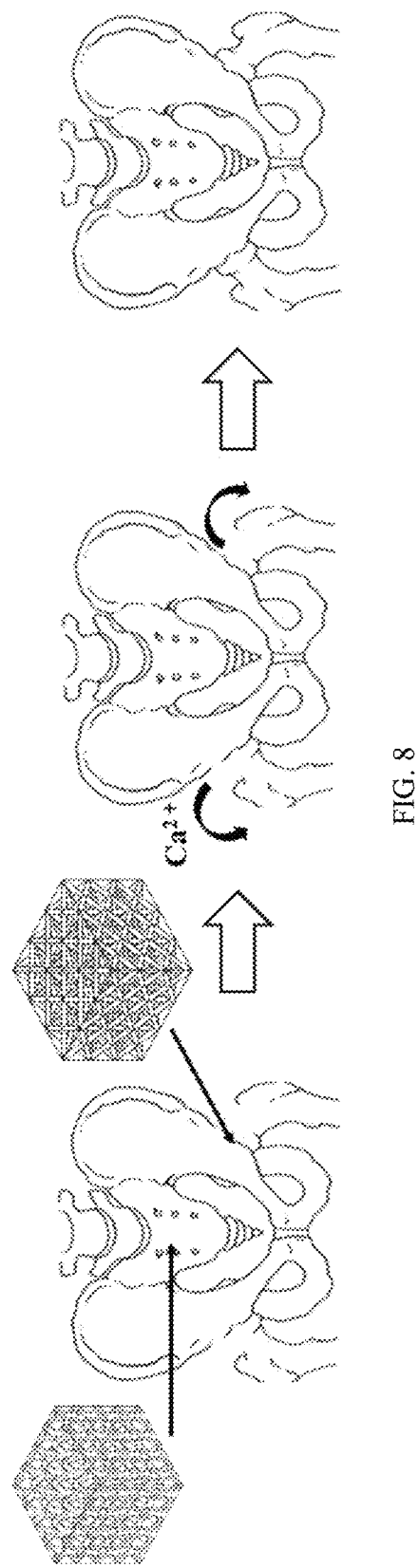
FIG. 8 is a healing effect diagram of bone implantation.

As shown in FIG. 8, when the human pelvic bone or hip joint is subjected to significant impact or trauma, the bone surface may generate cracks or even gaps, and in order not to affect the normal life, it is necessary to perform hip joint and pelvic bone replacement for bone repair. The titanium-magnesium interpenetrating phase composite structure prepared by the above two methods is used to replace or fill the gaps and injuries, and suture after filling. After implantation into the human body, the hydroxyapatite coating on the surface of titanium-magnesium interpenetrating phase composite structure can effectively slow down the corrosion of magnesium and prevent the premature degradation of the implant due to the corrosion of body fluids, thus affecting the bone repair process; on the other hand, the calcium and phosphorus plasma released after the degradation of hydroxyapatite coating can help promote the development of chondrocytes and the formation of bone trabeculae; the surface of hydroxyapatite coating will induce the deposition of new bone new bone promote the reaction between osteoblasts and osteoclasts, make them adhere to the surface of hydroxyapatite coating for growth, induce the growth of bone tissues along the implantation interface, and cooperate with rehabilitation training after implantation. The damaged bone gap can gradually heal, compared with the previous single metal implant material, shorten the bone formation cycle and greatly reduce the suffering of patients.

The invention claimed is:

1. A method for preparing a heterogeneous metal composite structure for medical implantation, comprising the steps of:
    step 1, preparing, based on a selective laser melting technique or a laser powder bed fusion technique, titanium alloy powder (7) into a porous skeleton (2) according to different printing strategies,
    step 2, filling magnesium after being melted into pores of the porous skeleton (2), and
    step 3, cooling a titanium-magnesium interpenetrating phase composite structure prepared in step 2 to room temperature, and covering a surface of the titanium-magnesium interpenetrating phase composite structure with a hydroxyapatite coating, wherein
    in step 1, the porous skeleton (2) has a lattice dot-array structure;
    the lattice dot-array structure is a body-centered cubic dot-array structure, a closed tetragonal beam-0 type structure or a closed arc beam-0 type structure;
    the body-centered dot-array structure is a hexahedron with eight vertices as key nodes, which are connected to each other to form external beams, and centers of the six faces serve as nodes of internal beams, and the internal beams are connected to and combined with the external beams to form a body-centered cubic structure;
    the closed tetragonal beam-0 type structure is based on a face-centered lattice to construct diagonal X-beams, middles of which are fixed using straight columns, and a base configuration is constructed by mirroring 2-3 times, joints between the diagonal X-beams are at the face centers of each plane, and the closed tetragonal beam-0 type structure is built by regulating a total horizontal length a and a vertical length b;
    the closed arc beam-0 type structure is based on a quadrilateral, with four sides cut with circular arcs, constructing arc beams for circular arrays to establish the closed arc beam-0 type structure, in which a horizontal arc diameter C1 and a vertical arc C2 are used as variable parameters to regulate the porosity of the closed arc beam-0 type structure; and
    by printing multiple lattice dot-array structures for different impact conditions and filling the same according to different stress regions of a pelvis, the closed arc beam-0 type structure is arranged in a sacral region; the body-centered cubic dot-array structure is arranged in an acetabular region; and the closed tetragonal beam-0 type structure is arranged in an iliac region, for connecting the sacral region and the acetabular region; wherein the different stress regions comprise the sacral region, the acetabular region, and the iliac region; the different impact conditions comprise a largest bearing capacity, a good vibration damping performance, and a stability in deformation and effectively transmitting loads;
    wherein in step 1, the porous skeleton (2) is prepared using the selective laser melting technique by a following specific method: purging, before printing, a material molding chamber of a selective laser melting device (6) with high-purity argon gas until oxygen content in the molding chamber is less than 0.1%, preheating a print substrate to 200° C., ensuring a dimensional accuracy for printing the porous skeleton (2), continuously printing the titanium alloy powder (7) with a median diameter of 35 µm in layers using the selective laser melting technique under the conditions of a laser power of 100 W, a laser scanning speed of 1200 mm/s, and a layer thickness of 30 µm;
    wherein in step 1, a specific method for preparing the porous skeleton (2) by using the laser powder bed fusion technique is as follows: processing the titanium alloy powder (7) with the median diameter of 35 µm by adopting the laser powder bed fusion technique with a laser powder bed device (11) with process parameters of the scanning speed of 1200 mm/s and the laser power of 155 W, reducing, during a scanning process, a thermal stress between two adjacent layers by using a sawtooth pattern, and alternating a scanning angle by 90° on a previous layer.

2. The method for preparing a heterogeneous metal composite structure for medical implantation according to claim 1, wherein in step 2, the specific method for filling magnesium after being melt into pores of the porous skeleton (2) is as follows: placing the printed porous skeleton (2) on a stainless steel mold (3), placing a magnesium block (1) on the porous skeleton (2) in a smooth manner, and placing the stainless steel mold (3) on a fixing apparatus (4) in a graphite resistance furnace (5), to complete the preparatory work before the infiltration, wherein it is ensured that an actual height of the stainless steel mold (3) is higher than a plane of the magnesium block (1), the graphite resistance furnace (5) is heated to 800° C. by heating in the flow of argon for 10 min, during which, the molten magnesium block (1) flows into the pores of the porous skeleton (2) by its own gravity in the absence of external loads, and is cooled in the graphite resistance furnace (5) to complete the infiltration process.

3. The method for preparing a heterogeneous metal composite structure for medical implantation according to claim 1, wherein in step 2, the specific method for filling magnesium after being melt into pores of the porous skeleton (2) is as follows: placing the prepared porous skeleton (2) in an alumina ceramic mold (10), evenly sprinkling the magnesium powder (9) inside pores of the porous skeleton (2), allowing the magnesium powder (9) to be fully filled into internal pores of the porous skeleton (2) by means of mechanical vibration, smoothly placing the alumina ceramic mold (10) in a hot isostatic pressing sintering furnace (8), vacuuming the hot isostatic pressing sintering furnace (8) and introducing argon gas, mixing the porous skeleton (2) and the magnesium powder (9) using a hot isostatic pressing process, and heating the hot isostatic pressing sintering furnace (8) in an argon environment in the pressure of 150 Mpa for 4 h to 900° C., heating 150 MPa pressure for 4 hours, the magnesium powder (9) being melted during the heating, and being closely adhered to the porous skeleton (2) under the pressure and temperature.

4. The method for preparing a heterogeneous metal composite structure for medical implantation according to claim 2, wherein in step 3, the specific method for covering a surface of the titanium-magnesium interpenetrating phase composite structure with a layer of hydroxyapatite coating is as follows: preparing the hydroxyapatite coating using an electrophoretic deposition method;

using the prepared titanium-magnesium interpenetrating phase composite structure as a negative electrode, and an inert electrode graphite sheet as a positive electrode, with two pole sheets of negative electrode and positive electrode kept parallel and a distance between the negative electrode and the positive electrode being at 20 mm, vertically inserting the titanium-magnesium interpenetrating phase composite structure into a quartz glass beaker with an HA suspension, adding 2% of a volume fraction of concentrated nitric acid as an electrolyte, adjusting a pH value with ammonia to stabilize the pH value at the range of 4-6, performing electrolytic deposition under a constant-voltage mode for a certain period of time under a set voltage, covering the surface of the titanium-magnesium interpenetrating phase composite structure as the negative electrode by the hydroxyapatite coating during deposition, closing a power source after the surface of the titanium-magnesium interpenetrating phase composite structure is completely covered with the hydroxyapatite coating, and taking out a sample for drying.

5. The method for preparing a heterogeneous metal composite structure for medical implantation according to claim 3, wherein in step 3, the specific method for covering a surface of the titanium-magnesium interpenetrating phase composite structure with a layer of hydroxyapatite coating is as follows: preparing the hydroxyapatite coating using an electrophoretic deposition method;

using the prepared titanium-magnesium interpenetrating phase composite structure as a negative electrode, and an inert electrode graphite sheet as a positive electrode, with two pole sheets of negative electrode and positive electrode kept parallel and a distance between the negative electrode and the positive electrode being at 20 mm, vertically inserting the titanium-magnesium interpenetrating phase composite structure into a quartz glass beaker with an HA suspension, adding 2% of a volume fraction of concentrated nitric acid as an electrolyte, adjusting a pH value with ammonia to stabilize the pH value at the range of 4-6, performing electrolytic deposition under a constant-voltage mode for a certain period of time under a set voltage, covering the surface of the titanium-magnesium interpenetrating phase composite structure as the negative electrode by the hydroxyapatite coating during deposition, closing a power source after the surface of the titanium-magnesium interpenetrating phase composite structure is completely covered with the hydroxyapatite coating, and taking out a sample for drying.

* * * * *